US012782332B2

(12) United States Patent
Ossapofsky

(10) Patent No.: US 12,782,332 B2
(45) Date of Patent: Nov. 3, 2026

(54) APPARATUS AND METHOD FOR MONITORING INERTING

(71) Applicant: Pilz GmbH & Co. KG, Ostfildern (DE)

(72) Inventor: Reinhold-Johannes Ossapofsky, Ostfildern (DE)

(73) Assignee: Pilz GmbH & Co. KG, Ostfildern (DE)

( * ) Notice: Subject to any disclaimer, the term of this patent is extended or adjusted under 35 U.S.C. 154(b) by 437 days.

(21) Appl. No.: 18/486,539

(22) Filed: Oct. 13, 2023

(65) Prior Publication Data

US 2024/0125750 A1 Apr. 18, 2024

(30) Foreign Application Priority Data

Oct. 13, 2022 (DE) ........................ 10 2022 126 773

(51) Int. Cl.
*G01N 33/00* (2006.01)
*F01N 11/00* (2006.01)

(52) U.S. Cl.
CPC ......... *G01N 33/0062* (2013.01); *F01N 11/00* (2013.01); *G01N 33/005* (2013.01); *F01N 2560/024* (2013.01); *F01N 2900/1411* (2013.01)

(58) Field of Classification Search
CPC .. G01N 33/0062; G01N 33/005; F01N 11/00; F01N 2560/024; F01N 2900/1411
See application file for complete search history.

(56) References Cited

U.S. PATENT DOCUMENTS

| | | | | |
|---|---|---|---|---|
| 2008/0057686 | A1 | 3/2008 | Melgaard | |
| 2015/0330631 | A1* | 11/2015 | Amikura | F23M 11/00 137/6 |
| 2018/0239374 | A1 | 8/2018 | Doore et al. | |
| 2021/0106955 | A1* | 4/2021 | Matsushima | G03F 7/70858 |

FOREIGN PATENT DOCUMENTS

| | | | |
|---|---|---|---|
| DE | 102005034396 | A1 | 1/2007 |
| DE | 102008013150 | A1 | 9/2009 |
| DE | 102012003278 | A1 | 8/2013 |
| DE | 102017123999 | A1 | 4/2019 |

* cited by examiner

*Primary Examiner* — Nathaniel T Woodward
(74) *Attorney, Agent, or Firm* — Miller Johnson

(57) ABSTRACT

An apparatus for monitoring inerting in an exhaust gas discharge of a production facility includes a first flow measuring unit; a second flow measuring unit, and a monitoring unit. The first flow measuring unit is connectable to a first flow meter arranged in a first supply line of a first gas to the production facility and the second flow measuring unit is connectable to a second flow meter arranged in a second supply line of a second gas to the exhaust gas discharge. The first flow measuring unit determines a first gas quantity supplied to the production facility and the second flow measuring unit determines a second gas quantity of the second gas supplied to the exhaust gas discharge. The monitoring unit triggers a safety-related control function based on the determined first and second gas quantity.

18 Claims, 3 Drawing Sheets

APPARATUS AND METHOD FOR MONITORING INERTING

CROSS-REFERENCE TO RELATED APPLICATIONS

This application claims priority to German Application No. 10 2022 126 773 filed Oct. 13, 2022, the entire disclosure of which is incorporated by reference.

FIELD

The present disclosure relates to an apparatus and method for monitoring inerting.

BACKGROUND

Inerting generally refers to a process in which the addition of an inert gas, i.e., the addition of gas sluggish in reaction, to a volume prevents the formation of an explosive mixture within the volume. Inerting of rooms for fire and explosion protection is known and is used, among other things, for chemical storage facilities, production plants and in aircraft construction.

App. No. DE 10 2008 013 150 A1 shows, for example, a system for inerting a gas volume in an aircraft, in which two exhaust gases are mixed to form an inert gas and then are added to a gas volume to be inerted. The inert gas displaces or dilutes reactive gases in the gas volume so that they no longer pose a danger. The system checks whether sufficient inerting has taken place by a measuring probe that is arranged in the gas volume to be inerted and which determines the chemical and material composition of the gas volume after the inert gas has been introduced. If the determined gases in the inerted gas volume correspond to a defined ratio, sufficient inerting is assumed.

In the semiconductor industry, special production facilities, simply known as "tools", are used to produce semiconductor components. The production facilities usually have an enclosed chamber in which the semiconductor elements are assembled. Process gases are introduced into the chamber for various operations that either directly serve to build the semiconductor element or provide a manufacturing environment needed for the fabrication of the semiconductor element. The process gases are removed from the chamber and transferred to an exhaust tract, once a manufacturing step or the semiconductor element is completed.

The process gases may contain toxic or highly reactive gases that must be adequately neutralized in the exhaust tract. For example, hydrogen can be used as a process gas that mixes with the oxygen in the air and may cause an oxyhydrogen reaction when ignited. Depending on how the tool is designed and the integrated safety functions it brings along, the introduced hydrogen may be discharged again up to 100% at the output of the tool. Since not all semiconductor production facilities (Fabs) have an explosion-proof exhaust tract (Exhaust) or the tools themselves are designed for residual hydrogen removal, measures must be taken to protect people and machinery to eliminate an explosion risk posed by reactive gases.

One possibility for this is to carry out inerting within the exhaust tract, in which the discharged hydrogen is diluted with sufficient inert gas (e.g. nitrogen) in the form of purging, or any oxygen that may be present is displaced, so that a hydrogen-oxygen concentration does not exceed the oxyhydrogen volume ratio of 2:1 (H2:O2) and there is no longer any risk of an oxyhydrogen reaction. In non-intelligent systems, the largest possible quantity of hydrogen introduced is determined and, based on this, a corresponding quantity of inert gas is added to the exhaust tract so that sufficient inerting can take place even in the case where up to 100% of the hydrogen introduced is discharged into the exhaust tract. This static process, however, consumes an unnecessarily large amount of inert gas. Intelligent systems, in turn, dynamically adjust the required amount of inert gas to the actual amount of hydrogen introduced or discharged. Accordingly, only the amount of inert gas actually required for inerting is introduced into the exhaust tract, which makes inerting more efficient. For safe operation of a dynamic inerting system, however, it is necessary that the inerting system is continuously monitored and that an appropriate reaction is triggered in the event of a malfunction, thus bringing the system or the exhaust tract into a safe state.

However, such monitoring requires that the various gases, or at least the gas components that are to be diluted or displaced by inerting, can be adequately determined. In practice, however, it has been shown that a probe in the volume to be inerted, as shown, for example in the DE 10 2008 013 150 A1, cannot be used easily in an exhaust gas tract of a production system. For example, simple probes for the determination of specific gas contents do not have the corresponding quality with regard to a detection accuracy or detection speed, or they are generally too susceptible to faults to be able to determine sufficient inerting with sufficient certainty. Special probes, on the other hand, which have a higher quality or are otherwise adapted to the special conditions in an exhaust tract, are regularly too expensive for an economical solution.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

It is an object to specify an apparatus and a method that enable improved monitoring of an inerting operation. Furthermore, it is an object to specify an apparatus and method that enable improved monitoring of an inerting operation in a safer, more flexible, and less expensive manner.

According to one aspect of the present invention, there is provided an apparatus for monitoring inerting in an exhaust gas discharge of a production facility, including: a first flow measuring unit; a second flow measuring unit; and a monitoring unit. The first flow measuring unit is connectable to a first flow meter arranged in a first supply line of a first gas to the production facility and the second flow measuring unit is connectable to a second flow meter arranged in a second supply line of a second gas to the exhaust gas discharge. The first flow measuring unit is configured to determine a first gas quantity of the first gas supplied to the production facility based on a measured value provided by the first flow meter and the second flow measuring unit is configured to determine a second gas quantity of the second gas supplied to the exhaust gas discharge based on a measured value provided by the second flow meter. The monitoring unit is configured to trigger a safety-related control function based on the determined first gas quantity and the determined second gas quantity.

According to another aspect of the present invention, there is provided a method for monitoring inerting in an exhaust gas discharge of a production facility, including:

providing a first flow measuring unit, a second flow measuring unit, and a monitoring unit, connecting the first flow measuring unit to a first flow meter disposed in a first supply line of a first gas to the production facility, connecting the second flow measuring unit to a second flow meter disposed in a second supply line of a second gas to the exhaust gas discharge, determining a first gas quantity of the first gas supplied to the production facility based on a measured value provided by the first flow meter, determining a second gas quantity of the second gas supplied to the exhaust gas discharge based on a measured value provided by the second flow meter, and triggering a safety-related control function as a function of the determined first gas quantity and the determined second gas quantity.

Thus, it is an idea to provide a monitoring apparatus that has two flow measuring units. A first flow measuring unit is connected to a flow meter within a supply line that provides a first gas for the process (process gas) within the production facility. The first flow measuring unit can continuously detect an amount of gas supplied to the production facility. In other words, the flow measuring unit determines the amount of gas introduced on the input side based on a flow measurement in a supply line of the gas to the production facility. A second flow measuring unit is connected to a flow meter arranged within a supply line to an exhaust tract of the production facility. The second flow measuring unit can continuously determine an amount of inert gas supplied to the exhaust tract. The second flow measuring unit determines the gas quantity based on a flow measurement in a supply line of the inert gas.

The two gas quantities determined can be set in relation to each other (defined ratio) in order to draw conclusions about the current inerting in the exhaust tract. By defining a value for a specific ratio as a threshold value, a reaction can be triggered if the defined ratio reaches, in particular falls below, this threshold value and insufficient inerting is to be assumed. For example, the detected gas quantities can correlate with a certain hydrogen-oxygen concentration and the defined threshold value can be a limit value for a critical hydrogen-oxygen concentration above which an explosive oxyhydrogen gas is present.

Thus, monitoring of inerting in the exhaust tract is done indirectly by determining the gas amounts supplied to both the production facility and the exhaust tract. This has the advantage that the monitoring apparatus can rely on simple flow meters. An actual concentration of the various gases in the exhaust tract does not need to be determined. The flow meters can be simple sensors, since they can be in supply lines that preferably carry only the gases to be measured. Consequently, only a volumetric flow rate needs to be measured without having to additionally determine the type or the concentration of the gas. Simple flow meters of various designs are known from the field of process technology for this purpose and are available at low cost. Indirect determination of inerting thus enables cost-effective and reliable determination of inerting even for intelligent systems that set inerting dynamically. The above-mentioned object is thus completely achieved.

In a further refinement, the apparatus may further include a processing unit configured to determine (calculate) from the first gas quantity determined by the first flow measuring unit a target value for the second gas quantity. Thereby, a process variable for inerting can be determined directly. In particular, the monitoring unit can be configured to perform the safety-related control function if the second gas quantity determined by the second flow measuring unit falls below the target value.

Preferably, the apparatus may include a flow rate control unit connectable to a flow rate controller arranged in the second supply line to the exhaust gas discharge, wherein the flow rate control unit is configured to control a gas supply of the second gas through the second supply line based on the first gas quantity determined by the first flow measuring unit, i.e. on the basis of a determined target value for the second gas quantity. The apparatus can thus be used not only for monitoring, but also directly for controlling inerting. Thus, even existing non-intelligent systems can be easily converted into intelligent systems with dynamic inerting by the proposed monitoring apparatus. Accordingly, the monitoring apparatus can be used very effectively.

The volume flow controller can have a maximum flow rate. A value of the maximum flow rate can be stored in the flow rate control unit. The processing unit can be configured to determine (calculate) a target value for the second gas quantity from the first gas quantity determined by the first flow measuring unit. Furthermore, the monitoring unit can be configured to trigger the safety-related control function if the determined target value exceeds the maximum possible flow rate. In the case of controlled inerting (dynamic inerting), monitoring can consequently be aligned with the control element used so that the safety-related control function (safety function) is triggered should the control element reach its limits. If, for example, the required amount of inert gas exceeds a possible flow rate that can be provided by the flow rate controller alone or by the system including the flow rate controller, this will also trigger the safety function. The safety of the entire system can thus be further increased.

The safety-related control function may include shutting down a supply of the first gas and/or shutting down the production facility as a whole. Both measures help to quickly and reliably transfer the production facility to a safe state in the event of erroneous or insufficient inerting. Advantageously, the safety-related control function can be limited to a single production facility without having to shut down other facilities that may be connected to the same exhaust tract. This refinement can thus advantageously contribute to a higher availability of the overall system.

The safety-related control function may include initiating an emergency flush, for instance by opening a bypass valve in the second supply line. Alternatively or additionally, the control function can also perform an emergency flush and use a bypass valve for this purpose, which is regularly available in corresponding systems, e.g. for manual flushing. The bypass valve may be a device independent of the actual control to adjust the supply to a maximum of the possible supply of inert gas. According to this refinement, safety can be further increased.

In one refinement, the first gas, i.e., the process gas of the manufacturing system, may include hydrogen and the inert gas may be nitrogen.

Furthermore, the processing unit and/or the monitoring unit can have a multi-channel, redundant design. Thereby, fail-safe execution of the monitoring and/or execution of the safety-related control function can be ensured to meet normative requirements. In addition, the processing unit and the monitoring unit can also have a diversified structure with different hardware. The redundant design enables constant testing of inputs and outputs as well as constant comparison of user data to ensure fail-safety.

It is understood that the above features and those to be explained below can be used not only in the combination indicated in each case, but also in other combinations or on their own, without departing from the scope of the present invention.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Figure 1:
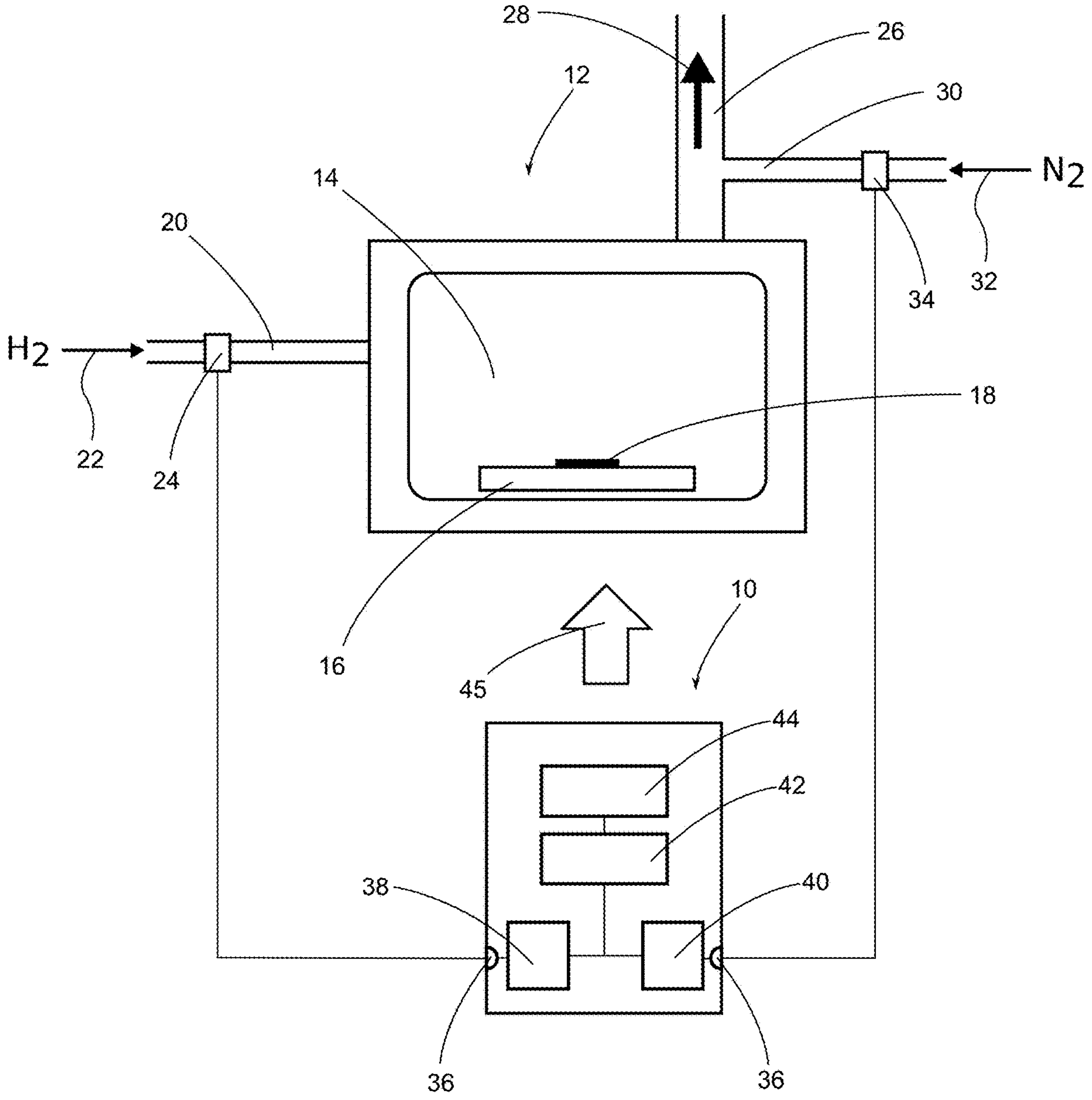
FIG. 1 is a schematic diagram of a production facility with an example of a monitoring apparatus for monitoring inerting.

FIG. 1 shows a production facility with an example of a monitoring apparatus. The monitoring apparatus is designated here in its entirety by reference numeral 10.

The production facility 12 is an example manufacturing system (tool) from the field of semiconductor manufacturing and is shown here in a highly simplified form. The production facility 12 has at least one chamber 14 in which the manufacturing process occurs. For example, a semiconductor substrate 18 may be placed on a slide 16 in chamber 14 for fabrication, and various mechanical and chemical fabrication steps may be performed on the substrate 18 to fabricate a semiconductor element.

The production facility 12 includes at least one supply line 20 through which a process gas 22 can be added for a fabrication step within the chamber 14. The process gas 22 may be used directly for chemical processing of the semiconductor element, or it may be a process gas that helps to create a working environment within the chamber 14 that is necessary for the manufacturing process. As indicated herein, the process gas 22 (first gas) may be hydrogen $H_2$.

A flow meter 24 is disposed in or on the supply line 20 of the process gas 22. The flow meter 24 may be of various types and may provide a value representing a gas supply of the process gas. In particular, the flow meter 24 may be a simple volumetric flow meter that determines a gas supply based on a volumetric flow rate, preferably without having to determine a concentration of the corresponding gas itself.

Further, the production facility 12 includes an exhaust tract 26 (exhaust gas discharge) through which the process gases introduced into the chamber 14 or any reaction products can be removed from the chamber 14. The discharged process gases or reaction products are referred to in the following simply as exhaust gases 28. Exhaust gases 28 may be actively or passively directed out of the chamber 14 into the exhaust tract 26.

A further supply line 30 is arranged to the exhaust tract 26, preferably at a position immediately after the exhaust tract 26 is led out of the production facility 12. Via the further supply line 30, an inert gas 32 can be supplied to the exhaust tract 26 in order to carry out inerting of the exhaust tract 26. In other words, an inert gas is introduced into the exhaust tract 26 to dilute the exhaust gases 28 or to displace certain gases that may be present in the exhaust tract. The inert gas 32 may be nitrogen $N_2$.

As in the supply line 20 for the process gas 22, a flow meter 34 is arranged in or on the further supply line 30. The further flow meter 34 may provide a value corresponding to a gas supply of inert gas. As with the flow meter 24 in the first supply line 20, the further flow meter 34 can be a simple volumetric flow meter.

The values of the flow meter 24 and the further flow meter 34 are fed to the monitoring apparatus 10, which has corresponding inputs 36. A first flow measuring unit 38 within the monitoring apparatus 10 can continuously determine a quantity of process gas (first gas quantity) that has been supplied to the chamber 14 based on the value provided by the first flow meter 24. At the same time, a second flow measuring unit 40 of the monitoring apparatus 10 may determine a quantity of inert gas (second gas quantity) that has been supplied to the exhaust tract 26. A processing unit 42 can put the gas quantities determined by the flow measuring units 38, 40 into a defined relation to each other. The defined ratio may represent a degree of inerting within the exhaust tract 26 resulting from the amounts of gas provided. For example, it is conceivable that the amounts of gas provided directly correlate to a hydrogen-oxygen concentration in the exhaust tract 26. In order to determine the defined ratio, the processing unit 42 may take into account at least one other parameter or include correction factors in the determination that are specific to the production facility 12, the exhaust tract 26, or the manufacturing process. Thereby, the monitoring apparatus can be flexibly adapted to different production facilities.

A monitoring unit 44 of the monitoring apparatus 10 may continuously compare the ratio determined by the processing unit 42 with a defined threshold value. The monitoring unit 44 triggers a safety-related control function when the determined ratio reaches the threshold. For example, the monitoring unit 44 triggers the safety-related control function if the determined ratio falls below the threshold value and, as a result, insufficient inerting in the exhaust tract 26 is to be assumed. The monitoring unit 44 thus triggers the safety-related control function depending on the determined gas quantities.

The safety-related control function 45 can avoid hazards posed by inadequate inerting. The safety-related control function 45 can differ depending on the type of production facility 12 or the process performed by the production facility 12. In one example, the safety-related function 45 may include shutting off a gas supply of the process gas in the supply line 20. Alternatively or additionally, the safety-related function 45 may result in a shutdown of the production facility 12 per se. Again, in another example, the safety-related control function 45 may include an active measures, such as triggering a separate purge of the exhaust tract 26. For such a purge, a bypass valve (not shown here) may be provided that allows a maximum inflow of inert gas into the exhaust tract 26, independent of any control of the amount of inert gas.

It is understood that the units described above, in particular the division into the various units, are to be understood purely functionally, and the individual units may also be integrated into one or more components. In one example, for instance, the flow measuring units 38, 40 the processing unit

42, and the monitoring unit 44 may be implemented by a central processing unit, such as a central processor (CPU), an ASIC, or a microcontroller.

Figure 2:
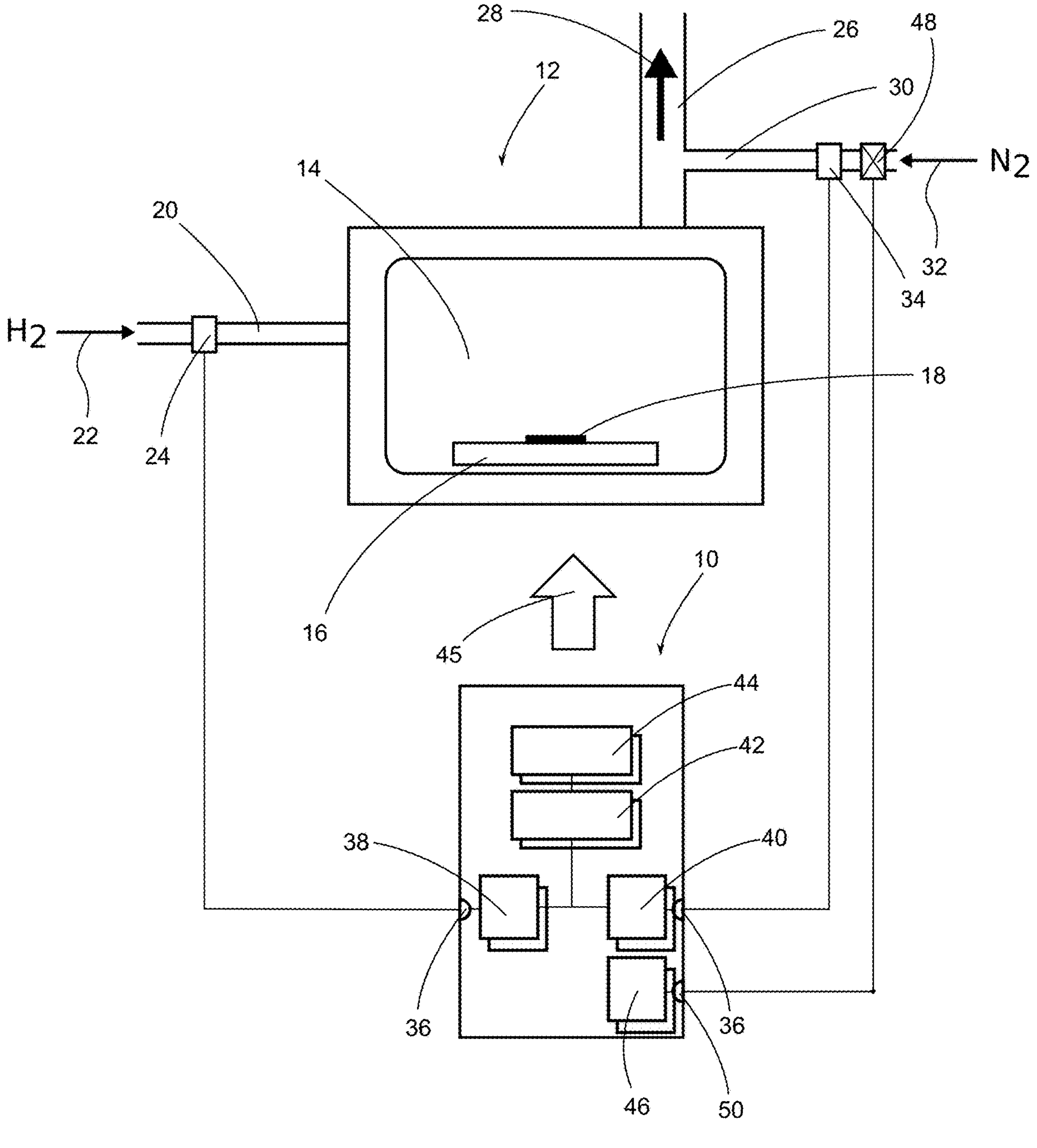
FIG. 2 is a schematic diagram of further variations of the monitoring apparatus according to FIG. 1.

Preferably, the individual units are integrated within a common housing to form a single functional control device that can be arranged in a control cabinet of the production facility 12. The control device may be a modular control device composed of individual hardware and software modules that implement the various tasks of the units described above. The modular control device can have a communication device, e.g. a module bus connecting the individual modules, via which the units are communicatively connected to each other. The control device can also be expandable and perform further control and regulation tasks. With reference to FIG. 2, various variations of the monitoring apparatus of FIG. 1 are explained in more detail.

FIG. 2 shows examples of various further refinements of the monitoring apparatus 10 described above, with the same reference signs denoting the same parts as before.

The monitoring apparatus 10 according to FIG. 2 differs from the monitoring apparatus 10 according to FIG. 1 inter alia by an additional flow rate control unit 46. The flow rate control unit 46 can be connected to a flow rate controller 48, which is arranged in the second supply line 30 upstream, i.e. in the flow direction upstream of the second flow meter 34. The flow rate controller 48 may be a controllable valve (MFC). In one example, the flow rate controller 48 may be, for example, a control valve with a medium-separated sensor and an integrated proportional integral (PI) controller. However, the invention is not limited to any particular type of flow rate controller. The flow rate controller 48 must only be capable of regulating a flow rate within the second supply line. Thus, the flow rate controller 48 is also not limited to a single device as shown in FIG. 2 but may include a combination of a plurality of different components that together regulate the flow rate.

The flow rate control unit 46 of the monitoring apparatus 10 controls the flow regulation. The flow rate control unit 46 may be integrated into the monitoring apparatus 10 in the same manner as the flow measuring units 38, 40 described above, with the difference that the flow rate control unit 46 is coupled to at least one output 50 of the monitoring apparatus 10, via which the flow rate control unit 46 may transmit a control signal to the flow rate controller 48.

The flow rate control unit 46 may control the flow rate controller 48 based on input from the processing unit 42. The input, in turn, is based on a value for the gas amount supplied to the production facility 12 via the first supply line 20, and thus is based on the value determined by the first flow measuring unit 38 (process gas amount). The input may correspond directly to the measured value, but may also take into account additional correction factors, tolerances, or otherwise transformations. Based on the input the supply of inert gas 32 through the second supply line 30 is controlled to ensure adequate inerting in the exhaust tract 26. In other words, the monitoring apparatus 10 dynamically adjusts the amount of inert gas to a required amount. For this purpose, the processing unit 42 may determine, based on the amount of process gas 22 introduced, a target value for the amount of inert gas 32 required to provide sufficient dilution or displacement in the exhaust tract 26. Based on the target value, the flow rate controller 48 is controlled via the flow rate control unit 46 and the inflow of inert gas is regulated.

In a specific example, when hydrogen is used as a process gas 22, a volume fraction of hydrogen in the exhaust tract may not exceed 3 vol %. Based on knowledge of the amount of hydrogen introduced and assuming that up to 100% can be discharged here into the exhaust tract, the processing unit 42 can determine, taking into account other parameters if necessary, an amount of inert gas 32 necessary to sufficiently dilute the discharged hydrogen in the exhaust tract 26 so that the critical volume fraction is not exceeded. The flow rate control unit 46 can then be used to control the supply of the inert gas. In addition to this control, the monitoring apparatus 10 can perform the monitoring of inerting described previously with respect to FIG. 1 and trigger a safety-related reaction if insufficient inerting is to be assumed.

The monitoring apparatus 10 according to FIG. 2 allows, in addition to the monitoring of the inerting described above, the monitoring of the control itself. For example, the monitoring unit 44 may also trigger the safety-related reaction when a target value determined by the processing unit 42 exceeds a maximum possible control condition. The maximum possible control condition may be limited, for example, by a maximum flow rate of the flow rate controller 48, the maximum possible feed pressure/diameter, etc., and may relate to the maximum amount of inert gas that can be conveyed through the supply line 30 by the flow rate controller 48. For instance, the safety-related reaction can be triggered in case the necessary target value cannot be reached. Furthermore, other factors that limit the inerting can be taken into account by additional threshold values.

The monitoring apparatus 10 is preferably a safety controller. A safety controller can perform control tasks in the same way as a normal controller, for example a programmable controller (PLC), in automation technology. In addition, however, a safety controller has further software and hardware facilities that can ensure fail-safe execution of certain control functions. The additional facilities include, for example, a multi-channel redundant design of the essential processing units and interfaces of the monitoring apparatus 10. This is indicated in FIG. 2 by the double representation of the individual units in each case.

In addition to a redundant design of the individual functional components of the safety controller, the components can also be diversified, e.g. by obtaining the redundant components from different manufacturers. Thereby, common cause faults can be effectively excluded, increasing intrinsic fault tolerance.

In addition to the monitoring of the inerting and its control described above, the safety controller can advantageously monitor other aspects, such as tolerance windows, tolerance times or dead times, in a fail-safe manner. The same applies to corrections of uncertainties due to deviations in the hardware design of the measured value acquisition, which can also be executed in a safety-related manner by a safety controller. Thus, safety can be further increased.

Figure 3:
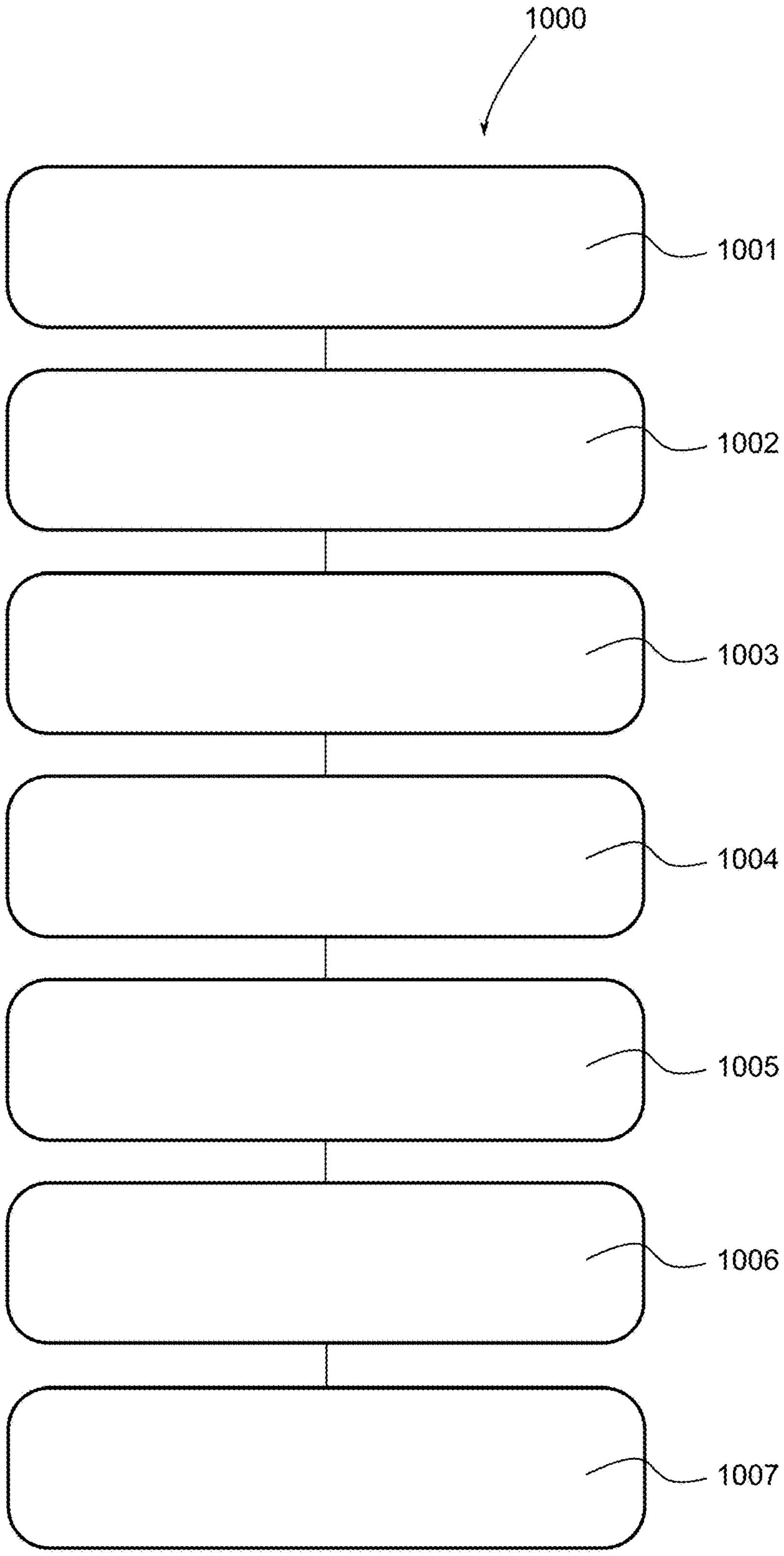
FIG. 3 is a schematic representation of an example of a method for monitoring inerting.

With reference to FIG. 3, an example of a method for monitoring inerting is described below. The method can be summarized as a method in which, in order to monitor inerting in an exhaust tract, a quantity of process gas supplied to a production facility and a quantity of inert gas supplied to the exhaust tract are continuously determined in order to determine a quantity ratio of these two gases in the exhaust tract by calculation and, as a function thereof, to trigger a safety-related control function when the quantity ratio assumes a critical value (threshold value).

Specifically, the process may have the steps indicated in FIG. 3. The method is designated in its entirety by reference numeral 1000.

In a first step 1001, a monitoring apparatus is provided. The monitoring apparatus has a processing unit, a first flow measuring unit, a second flow measuring unit, and a monitoring unit.

Next (step 1002), the first flow measuring unit is connected to a first flow meter disposed in a first supply line of a first gas to the production facility.

Further, the second flow measuring unit is connected to a second flow meter disposed in a second supply line of a second gas to the exhaust gas discharge (step 1003).

Thereafter, a first gas quantity of the first gas supplied to the production facility during operation of the facility based on a measured value provided by the first flow meter (step 1004) and a second gas quantity of the second gas supplied to the exhaust gas discharge based on a measured value provided by the second flow meter (step 1005) is determined. Preferably, the determination is carried out continuously after the production facility is started.

Finally, the determined gas quantities are used to determine the ratio in which they may be present to each other in the exhaust tract (step 1006), without explicitly measuring the actual concentration of the respective gases in the exhaust tract. Furthermore, in step 1007, a safety-related control function is triggered depending on the determined gas quantities, i.e. the monitoring unit triggers a safety-related control function if the ratio reaches a critical threshold value. The threshold value can be determined in advance by calculation or empirically, or it can be adjusted dynamically.

It is understood that the method is not limited to the examples shown here but may include other steps inserted before or after the individual steps. Similarly, individual steps can be repeated, in particular continuously, without this being explicitly indicated here.

The present invention is not limited by the embodiments or various implementations set forth herein but is defined solely by the following claims.

The term non-transitory computer-readable medium does not encompass transitory electrical or electromagnetic signals propagating through a medium (such as on a carrier wave). Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The phrase "at least one of A, B, and C" should be construed to mean a logical (A OR B OR C), using a non-exclusive logical OR, and should not be construed to mean "at least one of A, at least one of B, and at least one of C." The phrase "at least one of A, B, or C" should be construed to mean a logical (A OR B OR C), using a non-exclusive logical OR.

The invention claimed is:

1. An apparatus for monitoring inerting in an exhaust gas discharge of a production facility, the apparatus comprising:
- a first flow measuring unit;
- a second flow measuring unit;
- a processing unit; and
- a monitoring unit, wherein:
  - the first flow measuring unit is connectable to a first flow meter arranged in a first supply line of a first gas to the production facility,
  - the second flow measuring unit is connectable to a second flow meter arranged in a second supply line of a second gas to the exhaust gas discharge,
  - the first flow measuring unit is configured to determine a first gas quantity of the first gas supplied to the production facility based on a measured value provided by the first flow meter,
  - the second flow measuring unit is configured to determine a second gas quantity of the second gas supplied to the exhaust gas discharge for inerting based on a measured value provided by the second flow meter,
  - the monitoring unit is configured to trigger a safety-related control function in response to an inference of insufficient inerting, wherein the inference is made based on the first gas quantity and the second gas quantity, and
  - the processing unit is configured to determine a target value for the second gas quantity based on the first gas quantity.

2. The apparatus of claim 1 wherein the monitoring unit is configured to trigger the safety-related control function in response to the second gas quantity falling below the target value.

3. The apparatus of claim 1 further comprising:
- a flow rate control unit connectable to a flow rate controller disposed in the second supply line to the exhaust gas discharge,
- wherein the flow rate control unit is configured to control a gas supply of the second gas through the second supply line based on the first gas quantity.

4. The apparatus of claim 3 wherein:
- the flow rate controller has a defined maximum delivery rate; and
- the flow rate control unit is configured to store a value of the defined maximum delivery rate.

5. The apparatus of claim 4 wherein the monitoring unit is configured to trigger the safety-related control function in response to the target value exceeding the value for the defined maximum delivery rate.

6. The apparatus of claim 1 wherein the safety-related control function includes at least one of shutting off a supply of the first gas and shutting down the production facility.

7. The apparatus of claim 1 wherein the safety-related control function includes initiating an emergency flush.

8. The apparatus of claim 7 wherein the emergency flush includes opening a bypass valve in the second supply line.

9. The apparatus of claim 1 wherein the first gas includes hydrogen.

10. The apparatus of claim 1 wherein the second gas is an inert gas.

11. The apparatus of claim 10 wherein the inert gas is nitrogen.

12. The apparatus of claim 1 wherein the monitoring unit is of multi-channel redundant design.

13. A method for monitoring inerting in an exhaust gas discharge of a production facility, comprising:
- connecting a first flow measuring unit to a first flow meter disposed in a first supply line of a first gas to the production facility;
- connecting a second flow measuring unit to a second flow meter disposed in a second supply line of a second gas to the exhaust gas discharge;
- determining a first gas quantity of the first gas supplied to the production facility based on a measured value provided by the first flow meter;
- determining a second gas quantity of the second gas supplied to the exhaust gas discharge for inerting based on a measured value provided by the second flow meter;

triggering a safety-related control function in response to an inference of insufficient inerting, wherein the inference is based on the first gas quantity and the second gas quantity; and determining a target value for the second gas quantity from the first gas quantity.

14. The method of claim 13 further comprising triggering the safety-related control function in response to the second gas quantity falling below the target value.

15. The method of claim 13 further comprising:

controlling, by a flow rate control unit, a gas supply of the second gas through the second supply line based on the first gas quantity, wherein the flow rate control unit is connectable to a flow rate controller disposed in the second supply line to the exhaust gas discharge.

16. The method of claim 15 wherein:

the flow rate controller has a defined maximum delivery rate, and a value of the defined maximum delivery rate is stored in the flow rate control unit.

17. The method of claim 16 further comprising triggering the safety-related control function in response to the target value exceeding the value for the defined maximum delivery rate.

18. The method of claim 13 wherein the safety-related control function includes at least one of shutting off a supply of the first gas and shutting down the production facility.

* * * * *